United States Patent
Nakamura et al.

(10) Patent No.: US 6,564,092 B1
(45) Date of Patent: May 13, 2003

(54) TRANSDERMAL OR TRANSMUCOSAL DRUG DELIVERY DEVICE

(75) Inventors: Katsuhiro Nakamura, Tsukuba (JP); Kazuya Katagai, Tsukuba (JP); Kazutaka Inoue, Tsukuba (JP); Naruhito Higo, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/445,451

(22) PCT Filed: Jun. 25, 1998

(86) PCT No.: PCT/JP98/02847

§ 371 (c)(1),
(2), (4) Date: Mar. 27, 2000

(87) PCT Pub. No.: WO99/00157

PCT Pub. Date: Jan. 7, 1999

(30) Foreign Application Priority Data

Jun. 27, 1997 (JP) .............................................. 9/187623

(51) Int. Cl.[7] .............................................. A61N 1/30
(52) U.S. Cl. ..................... 604/20; 604/890.1; 604/289
(58) Field of Search ........................ 604/20, 289, 890.1, 604/19

(56) References Cited

U.S. PATENT DOCUMENTS 4,764,164 A  8/1988  Sasaki

FOREIGN PATENT DOCUMENTS

| EP | 138347 | 8/1984 |
|----|--------|--------|
| EP | 308572 | 8/1984 |
| JP | 2124176 | 5/1990 |
| JP | 767971 | 3/1995 |
| JP | 966111 | 3/1997 |

*Primary Examiner*—Brian L. Casler
*Assistant Examiner*—Jeremy Thissell
(74) *Attorney, Agent, or Firm*—Townsend & Banta

(57) ABSTRACT

A transdermal or transmucosal drug delivery device excellent in terms of drug permeability and skin irritability and capable of reducing power consumption, is disclosed. An output control circuit (4) of an energization pattern controller (1) supplies a combined energization of pulse depolarized type energization and at least one of direct current type energization and pulse energization between an anode-side device (5) and a cathode-side device (6) of iontophoresis. The details of combination of energization in the output control circuit (4) is determined based on external setting of the energization pattern controller (1) or internal storage information.

2 Claims, 2 Drawing Sheets

TRANSDERMAL OR TRANSMUCOSAL DRUG DELIVERY DEVICE

TECHNICAL FIELD

The present invention relates to a device for transdermal or transmucosal administration of drugs using iontophoresis, and particularly to a device to deliver drugs such as physiological active substances via the skin or mucosa such as the oral cavity and nasal cavity into a body using the principle of iontophoresis in the medical field.

BACKGROUND ART

Ointments, patches, or the like for transdermal and transmucosal administration, in addition to injections, oral preparations, and suppositories have conventionally been subjected to research and development as dosage forms of drugs such as physiological active substances. Transdermal and transmucosal administration has various advantages over the other administration methods, such as easiness in administration, maintenance of drug concentrations in blood, and avoidance of gastrointestinal adverse drug reactions. By transdermal and transmucosal administration, however, drugs are generally not absorbed well, and there are problems in absorption time and amount especially for drugs having a high molecular weight.

Various research and development efforts have been made on absorption-enhancing methods to increase drug absorption from the skin and mucosa. These methods include chemical enhancing methods using absorption-enhancing as well as physical enhancing methods using iontophoresis, phonophoresis, electrophoresis, or the like. Among these, in the case of iontophoresis, a drug is administered into a body via the skin or mucosa by applying voltage to the skin or mucosa to make an ionic drug migrate electrically.

Methods for energization applied for iontophoresis include direct current type energization, pulse type energization, and pulse depolarized type energization. Among these, pulse depolarized type energization has such advantages that it is excellent in terms of drug permeability over the direct current type and pulse type energization methods and that it gives only weak irritation on the skin and mucosa even applying a large electric current. The pulse depolarized type energization is described in, for example, Japanese Patent Laid-Open Publication No. 60-156475.

Since the pulse depolarized energization has the above-mentioned advantages, the method is quite useful for a device for iontophoresis. The present inventors faced a new problem, however, while we attempted practical application of a device, especially to obtain a small and portable device using this energization method. The problem is that the pulse depolarized energization consumes more electric power than the direct current type and pulse type energization methods. It is difficult to realize a reduction in device size and to obtain a portable device without solving this problem.

Therefore, it is an object of the present invention to provide a transdermal or transmucosal drug delivery device excellent in terms of drug permeability and skin irritability and capable of reducing electric power consumption.

DISCLOSURE OF THE INVENTION

The above objective can be accomplished by a transdermal or transmucosal drug delivery device configured so as to combine the pulse depolarized type energization (pulse depolarized direct current type energization) and at least one of direct current type energization and pulse type energization (pulse direct current type energization).

The combined energization was experimentally found by the present inventors, and any combination of the pulse depolarized type energization with other energization methods has not been attempted yet. It has been generally considered that such a combination that a part of the pulse depolarized type energization is replaced by other energization methods may reduce electric power consumption, but advantages in terms of drug permeability and skin irritability may also be reduced. However, experiments by the present inventors revealed that the above combinations of energization methods can drastically reduce electric power consumption with maintaining the effects in terms of drug permeability and skin irritability equally or at some degree. Then, repeated implementations of energization of these combinations could provide a greater effect. The details of the combined energization are determined by external setting of a device or based on the internal storage information.

Now, the direct current type energization supplies a predetermined direct current between electrodes, and the pulse type energization supplies predetermined repetitive pulses between electrodes. Although the pulse depolarized type energization supplies predetermined repetitive pulses between electrodes, like the pulse type energization, a residual charge is forced to be discharged during a pulse-resting phase, unlike the pulse type energization. These energization patterns can be provided by an energization pattern controller that generates a combined output comprising pulse depolarized output and at least one of direct current output and pulse output.

BEST MODE FOR CARRYING OUT THE INVENTION

Figure 1:
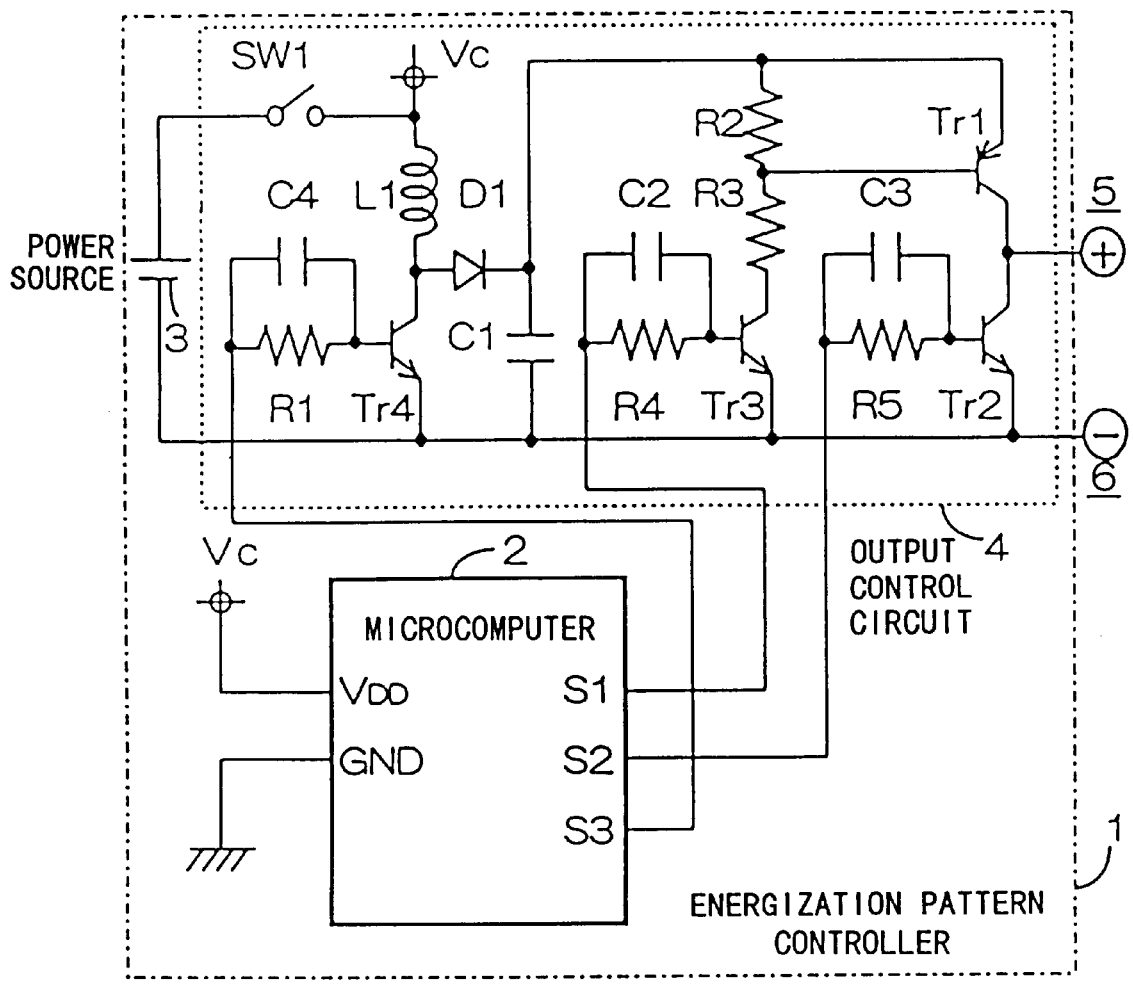
FIG. 1 is a circuit diagram showing a configuration of a drug delivery device according to the present invention.

FIG. 1 shows a circuit diagram showing a configuration of a drug delivery device according to the present invention. The device comprises an energization pattern controller 1 and is connected to an anode-side device 5 and a cathode-side device 6. The energization pattern controller 1 comprises a microcomputer 2, a power source 3, and an output control circuit 4.

In the output control circuit, Tr1 to Tr4 denote transistors, D1 denotes a diode, C1 to C4 denote capacitors, and R1 to R5 denote resistor. SW1 is a slide-type power switch, and sliding the switch turns on and off power.

L1 is a coil to increase source voltage. Oscillation of signal S3 from a microcomputer 2 generates a back electromotive force in the coil L1. A voltage higher than the source voltage can be obtained by accumulating the back electromotive force in the capacitor C1 through the diode D1.

Tr1 is an output transistor to supply electrical charge accumulated in the capacitor C1 to a load. Tr2 is an output transistor to recover electrical charge accumulated in the load upon pulse depolarization. Tr3 is a transistor to drive Tr1, and is employed as a level converter for a control signal when an output voltage is higher than the source voltage of the microcomputer 2.

In this configuration, switching among the pulse depolarized energization, pulse energization, and direct current energization can be controlled by the microcomputer.

The pulse depolarized output can be achieved by oscillating an output control signal S1 at any frequency and making an output control signal S2 a reverse phase against the output control signal. For example, when S1 is "High," S2 is "Low," and then output is "High." When S1 is "Low." S2 is "High," and then output is "Low."

Pulse output is carried out by oscillating the output control signal S1 at any frequency and fixing the output control signal S2 at "Low."

Direct current output is carried out by fixing the output control signal S1 at "High" and the output control signal S2 at "Low."

In this configuration, the pulse depolarized output, pulse output, and direct current output are switched under microcomputer control. However, the present invention is not limited to this embodiment and optional selection is allowed.

Switching and repeating of outputs can be preprogrammed under microcomputer control, or can be optionally set by users by providing an external switch. The energization controller thus provides between the respective electrodes for iontophoresis with various energization patterns.

The energization patterns employed according to the present invention comprises combination patterns comprising 2 or more patterns containing at least pulse depolarized type energization among these 3 types of energization. These can be implemented according to various embodiments below:

1) Pulse depolarized type energization followed by direct current type energization;
2) Pulse depolarized type energization followed by pulse type energization;
3) Pulse depolarized type energization followed by direct current type energization followed by pulse type energization;
4) Pulse depolarized type energization followed by pulse type energization followed by direct current type energization;
5) Direct current type energization followed by pulse depolarized type energization;
6) Direct current type energization followed by pulse type energization followed by pulse depolarized type energization;
7) Direct current type energization followed by pulse depolarized type energization followed by pulse type energization;
8) Pulse type energization followed by pulse depolarized type energization;
9) Pulse type energization followed by direct current type energization followed by pulse depolarized type energization;
10) Pulse type energization followed by pulse depolarized type energization followed by direct current type energization; and
11) Repeat (1) to (10), respectively.

Among various embodiments above, it is preferable to repeat the combination (1) or (5).

The energization duration was from 1 μsec to 60 minutes, preferably 10 μsec to 10 minutes for pulse depolarized energization. Energization duration less than 1 μsec cannot provide the effects of pulse depolarized energization fully and results in lower drug permeability and higher skin irritability, while that exceeding 60 minutes cannot provide a sufficient reduction in power consumption.

The ratio of application duration between the pulse depolarized energization and other types of energization is from 100:1 to 1:100, preferably from 10:1 to 1:10 for a combination of two types of energization; and from 100:1:1 to 1:100:100, preferably from 10:1:1 to 1:10:10 for a combination of three types of energization. When two types of energization are employed, a ratio of pulse depolarized energization higher than 100:1 cannot provide a sufficient reduction in power consumption, and a ratio of pulse depolarized energization lower than 1:100 cannot provide sufficient effects of pulse depolarized energization and results in lower drug permeability and higher skin irritability. When 3 types of energization are employed, a ratio of pulse depolarized energization higher than 100:1:1 cannot provide a sufficient reduction in power consumption, and a ratio of pulse depolarized energization less than 1:100:100 cannot provide sufficient effects of pulse depolarized energization and results in lower drug permeability and higher skin irritability.

When a combination of various types of energization is repeated, resting duration between the respective energization methods or the number of repeating is not restricted.

Thus, according to the present invention, the energization methods exemplified above can deliver drugs efficiently via the skin and mucosa and reduce power consumption.

The energization method according to the present invention does not cause skin irritation, because reversible or irreversible dielectric breakdown of the skin is not caused, unlike in electroporation.

The applied electric current in iontophoresis by the pulse depolarized energization according to the present invention is in the range of 0.001 to 10 $mA/cm^2$, preferably 0.01 to 1 $mA/cm^2$, and the applied voltage is in the range of 0.01 to 50 V, preferably 0.1 to 30V, more preferably 1 to 20 V. Applied electric current less than 0.001 $mA/cm^2$ or applied voltage less than 0.01 V results in lower drug permeability, whereas applied electric current exceeding 10 $mA/cm^2$ or applied voltage exceeding 50 V results in higher skin irritability.

The pulse frequency of the pulse depolarized type energization is in the range of 100 Hz to 1,000 kHz, preferably 1 to 500 kHz, and more preferably 10 to 100 kHz. Pulse frequency less than 100 Hz causes irritation to skin by energization, while that exceeding 1,000 kHz results in higher skin irritability. The duty is 10 to 90%, preferably 30 to 50%. Duty less than 10% results in lower drug permeability, and that exceeding 90% results in higher skin irritability.

The applied electric current in iontophoresis by the pulse type energization according to the present invention is about 0.001 to 10 $mA/cm^2$, preferably 0.01 to 1 $mA/cm^2$, and the applied voltage is in the range of 0.01 to 30 V, preferably 0.1 to 20 V, more preferably 1 to 10 V. The applied electric current less than 0.001 $mA/cm^2$ or applied voltage less than 0.01 V results in lower drug permeability and the applied electric current exceeding 10 $mA/cm^2$ or applied voltage exceeding 20 V results in higher skin irritability.

In addition, the pulse frequency is in the range of 100 Hz to 1,000 kHz, preferably 1 to 500 kHz, more preferably 10 to 100 kHz. The pulse frequency less than 100 Hz induces irritation by energization, and that exceeding 1,000 kHz results in higher skin irritation. The duty is 10–90%, preferably 30–50%. Duty less than 10% results in lower drug permeability, and that exceeding 90% results in higher skin irritability.

The applied electric current in iontophoresis by the direct current type energization according to the present information is about 0.001 to 10 mA/cm$^2$, preferably 0.01 to 1 mA/cm$^2$, and the applied voltage is in the range of 0.01 to 30 V, preferably 0.1 to 20 V, more preferably 0.1 to 10 V. The applied electric current less than 0.001 mA/cm$^2$ or applied voltage less than 0.01 V results in lower drug permeability, and the applied electric current exceeding 10 mA/cm$^2$ or applied voltage exceeding 20 V results in higher skin irritability.

Figure 2:
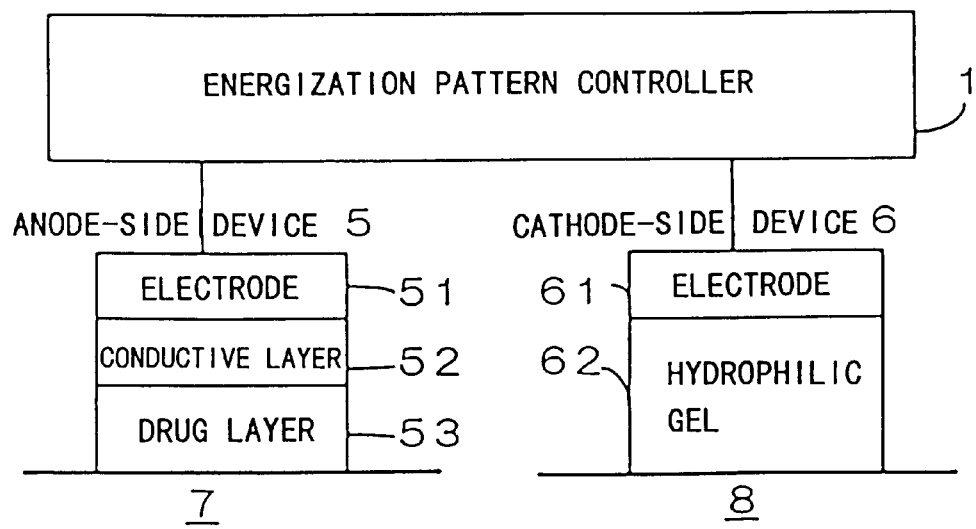
FIG. 2 is a drawing showing a drug delivery device according to the present invention closely attaching to the skin or mucosa.

FIG. 2 shows a drawing illustrating an anode side device 5 and a cathode side device 6 connected to an energization pattern controller 1 being in closely contact with the skin or mucosa 7 and 8. The anode side device 5 comprises an electrode 51, a conductive layer 52 and a drug layer 53 laminated on a base (not shown), and the cathode side device 6 comprises an electrode 61 and a hydrophilic gel 62 laminated on a base (not shown).

For the base, materials impermeable for at least drugs are employed to prevent leakage of the drugs. As the materials, for example, polyethylene, polypropylene, polyethylene terephthalate, polyvinyl chloride, polyvinylidene chloride, plasticized vinyl acetate copolymer, plasticized vinyl acetate-vinyl chloride copolymer, polyamide, cellophane, cellulose acetate, ethyl cellulose, and other plastic films and sheets are employed. These plastic films or sheets that are optionally laminated with aluminum foil, subjected to aluminum vapor deposition, or coated with ceramics may be employed.

The electrodes 51 and 61 are laminated on said base. Although lamination may be performed by coating or any other appropriate techniques, the electrodes are preferably laminated by print printing. As materials for the electrodes, both polarizing electrodes such as aluminum or its alloys, titanium or its alloys, iron or its alloys, and carbon, and non-polarizing electrodes such as silver, silver chloride, copper, copper chloride, or materials based on them such as silver/silver chloride (silver to which silver chloride is deposited, a mixture of silver and silver chloride, etc.), copper/silver chloride (copper to which silver chloride is deposited, a mixture of chloride and silver chloride) can be employed. Preferably, non-polarizing electrodes are employed. A preferred embodiment of combination is an electrode comprising a material based on silver or copper as the electrode 51 on the anode side and that based on silver chloride as the electrode 61 or copper chloride on the cathode side, and more preferably, an electrode comprising a silver-based material on the anode side and a silver chloride-based material on the cathode side and a silver chloride-based material on the cathode side is employed.

The conductive layer 52 is laminated on the electrode 51. Materials for the conductive layer are, for example, non-woven fabric, paper, gauze, absorbant cotton, porous materials, expanded materials, or the like composed of polyethylene, polypropylene, vinyl acetate, Nylon 66, polyolefin, polyamide, polyurethane, or the like, natural polysaccharides such as agar, karaya gum, locust bean gum, carageenan, gellan gum, tamarind gum, curdlan, pectin, farceran, guar gum, tara gum, tragacanth gum, xanthane gum, and polyvinyl alcohol and its partially saponified substances, polyvinyl formal, polyvinyl methyl ether and its copolymers, polyvinyl pyrrolidone, polyacrylic acid and its sodium salt, sodium alginate, water-soluble cellulose derivatives such as carboxymethyl cellulose and hydroxypropyl methyl cellulose, water-soluble macromolecules obtained by softening and plasticizing polyacryl amide, polyacryl amide derivatives, or the like with ethylene glycol, glycerin, or the like, as required, and its cross-linked hydrogels are employed. They are employed alone or in combination of 2 or more materials. Electrolytes, pH-adjusting agents, stabilizers, thickeners, wetting agents, surfactants, dissolution aids, absorption enhances, preservatives, ion-exchange resins, or the like may be added as required.

The drug layer 53 is laminated on the conductive layer 52, and a drug is impregnated or supported by a base material of the drug layer. As the base material, for example, non-woven fabric, paper, gauze, absorbant cotton, porous materials, expanded materials, or the like composed of polyethylene, polypropylene, vinyl acetate, Nylon 66, polyolefin, polyamide, polyurethane, or the like, can be employed.

As drugs such as physiologically active substances employed in the device for iontophoresis according to the present invention, centrally acting analgesics such as morphine, fentanyl, pethidine, codeine, buprenorphine, butorphanol, eptazocine, and pentazocine; peptides such as insulin, carcitonin, carcitonin-associated gene peptide, vasopressin, desmopressin, protirelin (TRH), adrenocorticotropic hormone (ACTH), luteinizing hormone-releasing factor (LH-RH), growth hormone releasing hormone (GRH), nerve growth factor (NGF), and other releasing factors, angiotensin, parathyroid hormone (PTH), thyroid stimulating hormone (TSH, thyrotropin), follicle stimulating hormone-releasing factor (FSH), luteinizing hormone (LH), prolactin, serum gonadotropic hormone, human chorionic gonadotropin (HCG), growth hormone, somatostatin, somatomedin, glucagon, oxytocin, gastrin, secretin, endorphin, enkephalin, endothelin, cholestokinin, neurotensin, interferons, interleukines, transferin, erythropoetin, superoxide dismutase (SOD), granulocyte stimulating factors (G-CSF), vassoactive intestinal polypeptide (VIP), muramyl peptide, corticotropin, urogastrone, and h-ANP; tranquilizers such as carbamazepine, chlorpromazine, diazepam, and nitrazepam; anti-neoplastics such as bleomycin, adriamycin, 5-fluorouracil, and mitomycin; tonics such as digitalis, digoxin, and digotoxin; sexual hormones such as estradiol and testosterone; anti-hypertensive agents such as reserpine and clonidine; local anesthetics such as lidocaine chloride, tetracaine chloride, procaine chloride, and dibucaine chloride; and steroids such as hydrocortisone sodium succinate, hydrocortisone sodium phosphate, prednisolone sodium succinate, betamethasone sodium phosphate, and dexamethasone sodium phosphate can be mentioned, but the drugs are not limited to these.

The hydrophilic gel 62 is laminated on the electrode 61. As materials for the hydrophilic gel 62, natural polysaccharides such as agar, karaya gum, locust bean gum, carageenan, gellan gum, tamarind gum, curdlan, pectin, farceran, guar gum, tara gum, tragacanth gum, xanthane gum, and polyvinyl alcohol and its partially saponified substances, polyvinyl formal, polyvinyl methyl ether and its copolymers, polyvinyl pyrrolidone, polyacrylic acid and its sodium salt, sodium alginate, water-soluble cellulose derivatives such as carboxymethyl cellulose and hydroxypropyl methyl cellulose, water-soluble macromolecules obtained by softening and plasticizing polyacryl amide, polyacryl amide derivatives, or the like with ethylene glycol, glycerin, or the like, as required, and its cross-linked hydrogels are employed.

The present invention shall be further illustrated by the following embodiments, but the present invention is not limited to the embodiments.

EXPERIMENTAL EXAMPLE 1

A permeability experiment was conducted in dogs. In this experiment, salmon carcitonin was administered to the oral mucosa of Beagle dogs. Blood was collected from the vein in the forefoot before the start of energization and at predetermined timings after energization and then centrifuged to obtain serum. Serum salmon carcitonin concentrations were determined by the radioimmunoassay (RIA) method.

Salmon carcitonin was administered as shown in FIG. 2 mentioned above. The anode side device 5 in this experiment comprises a laminate of a silver electrode, a conductive layer, and a drug layer containing salmon carcitonin and is attached under pressure to the oral mucosa of the Beagle dogs with a forceps made of an insulator. The cathode side device 6 comprises a laminate of a silver/silver chloride electrode and hydrophilic gel and is attached under pressure to the skin inside the ear of the Beagle dogs with a forceps made of an insulator. The contacting area between the anode side device 5 and the oral mucosa and that between the cathode side device 6 and the skin was 2.5 $cm^2$, respectively.

Energization was carried out with the energization pattern controller 1, while the amount of electric current was controlled at a constant level, and power consumption was obtained from applied voltage at that time. In the case of pulse depolarized type energization, electric current actually passing through the skin (applied electric current) was controlled, and power consumption was obtained from electric current applied on the skin (consumed electric current) and applied voltage.

After the completion of energization, the device was immediately removed, and primary irritation on the oral mucosa and the skin was observed and assessed according to the Criteria Table shown in Table 1.

TABLE 1

Criteria Table for Irritation Assessment

| Status of the mucosa or the skin | Score |
| --- | --- |
| Edema, papule | 2 |
| Apparent erythema | 1 |
| Mild erythema | 0.5 |
| Very mild erythema | 0.2 |
| No change | 0 |

EXAMPLE 1

A Combination of Pulse Depolarized Type Energization and Direct Current Type Energization In this Example 1, 200 μg of salmon calcitonin was dissolved in distilled water and injected into the drug layer in the anode side device 5. The anode side device 5 was attached to the oral mucosa and the cathode side device 9 to the skin, and then energization was started. Energization was conducted using a combination of pulse depolarized type energization and direct current type energization, at 0.2 mA for 5 minutes by pulsed depolarized type energization followed by at 0.2 mA for 10 minutes by direct current energization. This cycle was repeated 3 times. The frequency and the duty during pulse depolarized type energization were 30 kHz and 30%, respectively.

EXAMPLE 2

A Combination of Pulse Depolarized Type Energization and Pulse Type Energization In this Example 2, as in Example 1, the devices were attached to the oral mucosa and the skin, and then energization was started. Energization was conducted by a combination of pulse depolarized type energization and pulse type energization, at 0.2 mA for 5 minutes by pulse depolarized type energization followed by at 0.2 mA for 10 minutes by pulse type energization. This cycle was repeated 3 times. The frequency and the duty during pulse depolarized type energization were 30 kHz and 30%, respectively, and those during pulse type energization were 50 kHz and 50%, respectively.

COMPARATIVE EXAMPLE 1

Pulse Depolarized Type Energization

In this Comparative Example 1, as in Example 1, the devices were attached under pressure to the oral mucosa and the skin, and energization was started. Energization was conducted at 0.2 mA for 60 minutes using only pulse depolarized type energization. The frequency was 30 kHz and the duty was 30%.

Comparative Example 2

Direct Current Type Energization

In this Comparative Example 2, as in Example 1, the devices were attached under pressure to the oral mucosa and the skin, and energization was started. Energization was conducted at 0.2 mA for 60 minutes using only direct current type energization.

Test Results

Figure 3:
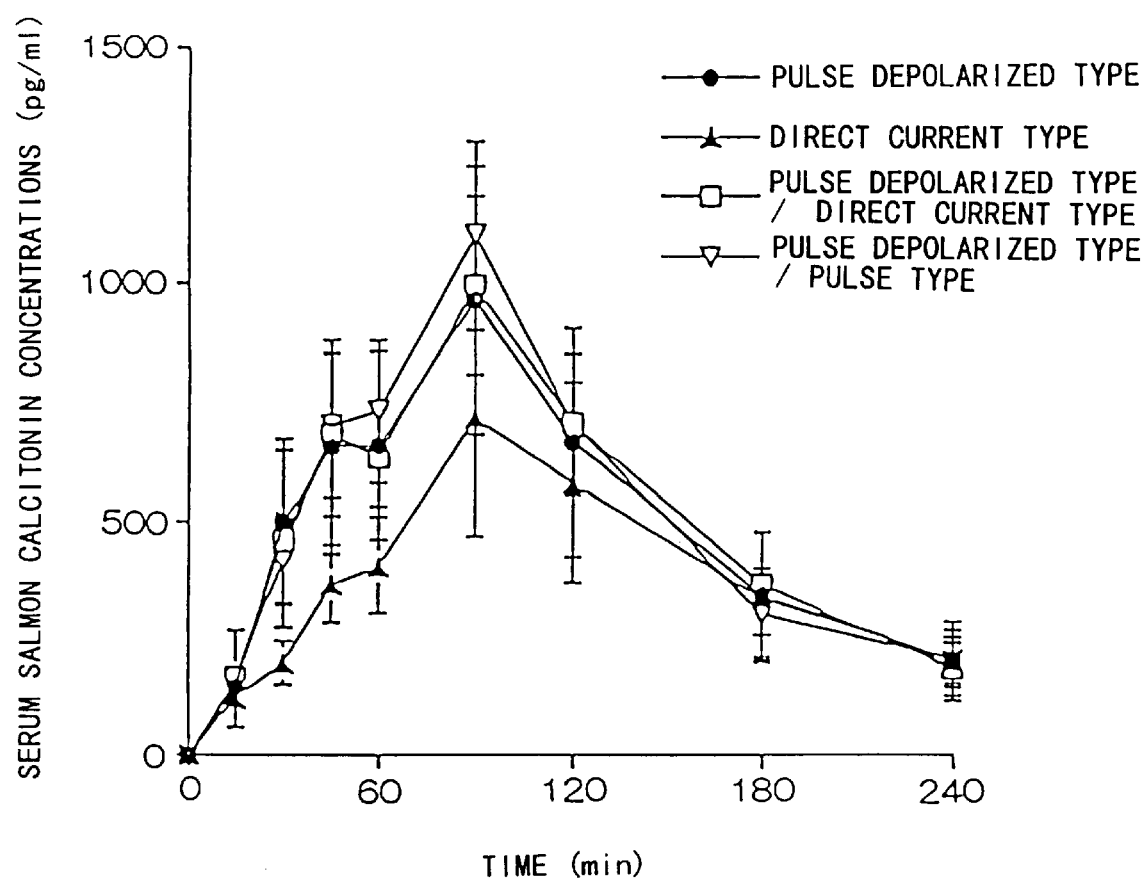
FIG. 3 is a graph showing the results of measurement of serum salmon calcitonin concentrations.

FIG. 3 shows the results of measurements of serum salmon carcitonin concentrations for Examples 1 and 2 and Comparative Examples 1 and 2. As shown in FIG. 3, the salmon carcitonin concentrations for the combination of pulse depolarized type energization and direct current type energization (Example 1) and the combination of pulse depolarized type energization and pulse type energization (Example 2) were almost equal to those for the pulse depolarized type energization alone (Comparative Example 1) and considerably higher than those for the direct current type energization alone (Comparative Example 2).

Table 2 shows the results of measurements of power consumption.

TABLE 2

Results of Measurements of Power Consumption

| | Energization method | Power consumption (mW) |
| --- | --- | --- |
| Example 1 | Pulse depolarized type energization/direct current type energization | 1.6 |
| Example 2 | Pulse depolarized type energization/pulse type energization | 1.5 |
| Comparative Example 1 | Pulse depolarized type energization | 95.7 |
| Comparative Example 2 | Direct current type energization | 0.6 |

As clearly shown in Table 2, the power consumption for the combination of the pulse depolarized type energization and direct current type energization (Example 1) and that for the combination of the pulse depolarized type energization and pulse type energization (Example 2), was slightly higher than that for the direct current type energization alone (Comparative Example 2) and drastically lower than that for the pulse depolarized type energization alone (Comparative Example 1).

Table 3 shows the results of assessment of primary irritation of the mucosa and the skin. The scores were obtained according to the Criteria Table shown in Table 1.

TABLE 3

Results of Assessment of Primary Irritation of the Mucosa and Skin

| | Energization method | Score (Average) | |
|---|---|---|---|
| | | Oral mucosa | Skin |
| Example 1 | Pulse depolarized type energization/direct current type energization | 0.23 | 0.13 |
| Example 2 | Pulse depolarized type energization/pulse type energization | 0.23 | 0.10 |
| Comparative Example 1 | Pulse depolarized type energization | 0.18 | 0.05 |
| Comparative Example 2 | Direct current type energization | 0.68 | 0.23 |

As clearly shown in Table 3, the skin irritability for the combination of the pulse depolarized type energization and direct current type energization (Example 1) and that for the combination of the pulse depolarized type energization and pulse type energization (Example 2) was slightly higher than that for the pulse depolarized type energization alone (Comparative Example 1) but drastically lower than that for the direct current type energization alone (Comparative Example 2).

As shown in the above test results, the use of combined energization according to the present invention provides such unexpected results that power consumption could be greatly reduced with keeping the effects of drug permeability and skin irritability in an equal level or in some degree as compared to the single use of pulse depolarized type energization.

INDUSTRIAL APPLICABILITY

The transdermal or transmucosal drug delivery device according to the present invention is excellent in terms of drug permeability and skin irritability and useful in reducing power consumption, thus suitable for the use in iontophoresis in the medical field.

What is claimed is:

1. A transdermal or transmucosal drug delivery device comprising: an energization pattern controller, configured so as to enable the drug delivery device to conduct energization by a combination of pulse depolarized type energization, direct current type energization, and pulse type energization, wherein the types of energization are conducted sequentially, either being followed by another type of energization directly or with resting duration between types of energization.

2. A transdermal or transmucosal drug delivery device comprising: an energization pattern controller, configured so as to enable the drug delivery device to conduct energization by a combination of pulse depolarized type energization, direct current type energization, and pulse type energization, wherein the types of energization are conducted sequentially, either being followed by another type of energization directly or with resting duration between types of energization, wherein the ratio of applied duration among said pulse depolarized type energization, direct current type energization, and pulse type energization is in the range of 100:1:1 to 1:100:100.

* * * * *